(12) United States Patent
Neuer et al.

(10) Patent No.: US 6,951,841 B2
(45) Date of Patent: *Oct. 4, 2005

(54) PHARMACEUTICAL COMPOSITIONS OF MACROLIDES OR CYCLOSPORINE WITH A POLYETHOXYLATED SATURATED HYDROXY-FATTY ACID

(75) Inventors: Klaus Neuer, Schwendl (DE); Monika Petszulat, Ulm (DE); Hatto Walch, Laupheim (DE)

(73) Assignee: Novartis AG, Basel (CH)

( * ) Notice: Subject to any disclaimer, the term of this patent is extended or adjusted under 35 U.S.C. 154(b) by 527 days.

This patent is subject to a terminal disclaimer.

(21) Appl. No.: 09/738,212

(22) Filed: Dec. 15, 2000

(65) Prior Publication Data

US 2001/0003589 A1 Jun. 14, 2001

Related U.S. Application Data

(63) Continuation of application No. 09/077,231, filed as application No. PCT/EP96/05279 on Nov. 28, 1996, now abandoned.

(30) Foreign Application Priority Data

Nov. 29, 1995 (DE) .......................................... 195 44 507

(51) Int. Cl.$^7$ .......................... A61K 38/00; A61K 37/18
(52) U.S. Cl. ............................ 514/11; 514/9; 514/613
(58) Field of Search ..................... 514/11, 9, 613; 424/456

(56) References Cited

U.S. PATENT DOCUMENTS

| | | | | |
|---|---|---|---|---|
| 3,288,824 | A | 11/1966 | Mahler et al. | 260/410.6 |
| 3,813,345 | A | 5/1974 | Urton | 252/312 |
| 3,954,967 | A | 5/1976 | Urton | 424/78 |
| 4,073,943 | A | 2/1978 | Wretlind et al. | 424/358 |
| 4,146,499 | A | 3/1979 | Rosano | 252/186 |
| 4,156,719 | A | 5/1979 | Sezaki et al. | 424/177 |
| 4,388,307 | A | 6/1983 | Cavanak | 424/177 |
| 4,567,161 | A | 1/1986 | Posanski et al. | 424/199 |
| 4,695,450 | A | 9/1987 | Bauer et al. | 424/168 |
| 4,719,239 | A | 1/1988 | Muller et al. | 514/785 |
| 4,794,000 | A | 12/1988 | Ecanow | 424/457 |
| 4,797,272 | A | 1/1989 | Linn et al. | 424/59 |
| 4,797,273 | A | 1/1989 | Linn et al. | 424/59 |
| 4,798,823 | A | 1/1989 | Witzel | 514/11 |
| 4,835,002 | A | 5/1989 | Wolf et al. | 426/590 |
| 4,888,239 | A | 12/1989 | Brox | 428/402.2 |
| 4,914,188 | A | 4/1990 | Dumont et al. | 530/317 |
| 4,963,367 | A | 10/1990 | Ecanow | 424/484 |
| 4,990,337 | A | 2/1991 | Kurihara et al. | 424/427 |
| 4,996,193 | A | 2/1991 | Hewitt et al. | 514/11 |
| 5,037,653 | A | 8/1991 | Dawson | 424/405 |
| 5,047,396 | A | * 9/1991 | Orban et al. | 514/11 |
| 5,154,754 | A | 10/1992 | Damo et al. | 71/DIG. 1 |
| 5,177,110 | A | 1/1993 | Oechslein et al. | |
| 5,206,219 | A | 4/1993 | Desai | |
| 5,260,301 | A | * 11/1993 | Nakanishi et al. | 514/291 |
| 5,338,761 | A | 8/1994 | Nakajima et al. | |
| 5,342,625 | A | * 8/1994 | Hauer et al. | 424/455 |
| 5,525,590 | A | 6/1996 | Bollinger et al. | |
| 5,639,724 | A | 6/1997 | Cavanak | 514/11 |
| 5,756,450 | A | 5/1998 | Hahn et al. | 514/9 |
| 5,759,997 | A | * 6/1998 | Cavanak | 514/11 |

FOREIGN PATENT DOCUMENTS

| | | |
|---|---|---|
| BE | 895724 | 7/1983 |
| CA | 1209361 | 8/1986 |
| CH | 641356 | 2/1984 |
| DE | 3316805 | 11/1984 |
| DE | 3924207 | 1/1990 |
| DE | 4418115 | 12/1994 |
| EP | 135171 | 3/1985 |
| EP | 170623 | 2/1986 |
| EP | 211258 | 2/1987 |
| EP | 258856 | 2/1988 |
| EP | 274431 | 7/1988 |
| EP | 314689 | 5/1989 |
| EP | 315 079 | 5/1989 |
| EP | 361928 | 4/1990 |
| EP | 0589843 | 3/1994 |
| EP | 705601 | 4/1996 |
| FR | 2553661 | 4/1985 |
| FR | 2642650 | 8/1990 |
| FR | 2678169 | 12/1992 |
| GB | 1171125 | 11/1969 |
| GB | 2098865 | 12/1982 |
| GB | 2206119 | 12/1988 |
| GB | 2209671 | 5/1989 |
| GB | 2211408 | 7/1989 |
| GB | 2211848 | 7/1989 |
| GB | 2218334 | 11/1989 |
| GB | 2221157 | 1/1990 |
| GB | 2222770 | 3/1990 |
| GB | 2224206 | 5/1990 |
| GB | 2228198 | 8/1990 |
| GB | 2230440 | 10/1990 |
| JP | 024776 | 4/1985 |
| JP | 249918 | 7/1986 |
| JP | 61280435 | 12/1986 |
| WO | 86/02264 | 4/1986 |
| WO | 87/01035 | 2/1987 |
| WO | 88/00059 | 1/1988 |
| WO | 90/08537 | 8/1990 |
| WO | WO 9112008 | 8/1991 |
| WO | 93/20833 | 10/1993 |
| WO | WO 9522982 | 8/1995 |
| WO | WO 9614079 | 5/1996 |

OTHER PUBLICATIONS

Board, P.G., FEBS Lett., vol. 315, No. 3, 298–300 (1993).
Carrigan et al., J. Pharm. Sci., 1973, vol. 62, pp. 1476–1479.
Cavanak and Suker, Prog. Allergy vol. 38:65–72 (1986).

(Continued)

*Primary Examiner*—Shaojia Anna Jiang
(74) *Attorney, Agent, or Firm*—Susan Hess

(57) ABSTRACT

Pharmaceutical compositions for oral administration comprising a cyclosporin or macrolide as active ingredient, and a polyethoxylated saturated hydroxy-fatty acid.

10 Claims, No Drawings

OTHER PUBLICATIONS

Anon., Research Disclosure 21143 (Nov. 1981), p. 420.
Beyer, et al., Pharmazie in unserer Zeit, vol. 12(2):55–60 (1983).
Bhargava, et al., Pharmaceutical Technology, 46–54, Mar. 1987.
Coon, et al., Cancer Res., vol. 51, No. 3, 897–902 (1991).
Chem. Abstr., 95:225610K, Anon. (1981).
Derwent Abst. 84/069426/12 (1984).
Derwent Abst. 92/235, 168/29 (1989).
Derwent Abst 92/216, 793/26 (1990).
Ekman, S., Lipids 22: 657–663 (1987).
Frazer, et al., J. Physiol. (1944) vol. 103, pp. 306–316.
Froemming, et al., Acta Pharm, Technol., vol. 36, No. 4, 214–220 (1990).
Hahn, Biodegradeble Tensides, 1–196, Basel University, Switzerland (1988) (Translation).
Jayakrishnan, et al., J. Soc. Cosmet, Chem. 34:335–350 (1983).
The Merck Index, 9th Ed., Merck & Co., Inc., Rahway, N.J. p. 1017 (1976).
Kraus, et al., Acta Pharm. Technol., vol. 36, No. 4, 221–225 (1990).
Mizushima, 86–335,072/51 (Apr. 26, 1985) (Derwent Abstr).
Mubarak, Development and Testing of New Microemulsions, 1–51 (1982) (Translation).
Muller, et al., Pharm. Ind. 50(11), 1305–1306 (1988).
Muller, et al., Pharm. Ind. 50(3): 370–375 (1988).
Pohler, Micro–Emulsion Gels Structural Investigations and Galenical Properties, 1–100 (1983) (Translation).
Remington's Pharmaceutical Sciences (17th ed.). Microemulsions, Chapter 20, pp. 293–300 (1985).
Reymond, In Vitro In Vivo Model for the Absorption of Cyclosporin A (1986) (Translation).
Reymond and Sucker, Pharmaceutical Research, vol. 5(10): 673–679 (1988).
Reymond et al., Pharmaceutical Research, vol. 5(10):677–679 (1988).
Ritschel, et al., Pharmaceutical Research vol. 5(10): PD 943: S–108 (1988).
Ritschel, et al., Methods and Findings in Experimental and Clinical Pharmacology, vol. 11(4):281–87 (1989).
Ritschel, et al., Methods and Findings in Experimental and Clinical Pharmacology, vol. 12, pp. 127–134 (1990).
W.A. Ritschel, Methods and Findings in Experimental and Clinical Pharmacology, vol. 13, pp. 205–220 (1991).
Takada, 87–024,776/04 (Apr. 4, 1985) (Derwent Abstr.).
Takada, et al., J. Pharmacobio–Dyn. vol. 8: 320–323 (1985).
Takada, et al., J. Pharmaceutical Research vol. 3(1): 48–51 (1986).
Takada, et al., J. Pharmacobio–Dyn. vol. 9: 156–160 (1986).
Takada, et al., J. Pharmacobio–Dyn. vol. 11:80–87 (1988).
Takada, et al., Intern'l Jour. of Pharmaceutics, vol. 44: 107–116 (1988).
Tarr, et al., Pharmaceutical Research, vol. 6(1): 40–43 (1989).
Yanagawa, et al., J. Microancapsulation 6(2): 161–164 (1989).
Ziegenmeyer, et al., Acta Pharmaceutical Technologica, vol. 26(4): 273–275 (1980).

* cited by examiner

PHARMACEUTICAL COMPOSITIONS OF MACROLIDES OR CYCLOSPORINE WITH A POLYETHOXYLATED SATURATED HYDROXY-FATTY ACID

This is a continuation of Ser. No. 09/077,231, May 26, 1998, abandoned which is a 371 of PCT/EP 96/05279, Nov. 28, 1996.

This invention relates to medicinal preparations for peroral administration containing a cyclosporin, especially cyclosporin A, or a macrolide, e.g. a rapamycin or an ascomycin, as pharmaceutically active agent.

Cyclosporins are cyclic oligopeptides of biological origin, which are used in particular as immunosuppressants. The cyclic polypeptide cyclosporin A consists of 11 amino acids. As a highly effective immunosuppressant, when tested on animals it prolongs the life of allografts, for example of skin, heart or kidneys. Research has shown that cyclosporin inhibits cell-linked reactions, the delayed hypersensitivity of the skin, graft-versus-host disease and T-cell-dependent antibody production. For this reason, cyclosporins are employed in organ transplants to prevent rejection reactions. Since, in contrast to other immunosuppressants, these compounds have only very low bone marrow toxicity, they are also used in the case of bone marrow transplants.

In addition, it is known that cyclosporins possess anti-inflammatory and anti-parasitic activity.

The use of the cyclosporins is therefore not restricted to immunosuppressants, but may be extended to the therapy of various auto-immune diseases and inflammatory conditions, especially also to the treatment of inflammatory disorders in which auto-immune processes play a role. These include arthritic illnesses, e.g. rheumatoid arthritis or other rheumatic disorders.

As anti-parasitic agents, cyclosporins may be used to treat protozoal infections such as malaria.

However, with the cyclosporin preparations that have been employed in practice for a long time, potentially serious side effects have had to be taken into account, in particular with regard to kidneys. In addition, It is known for example from E. Mutschler, Arzneimittelwirkungen, Lehrbuch der Pharmakologie und Toxikologie, Stuttgart, (1991), page 660, bottom right-hand column, that when administering cyclosporin or cyclosporin A orally, the bioavailability is only about 35%. Cyclosporins are substances of strongly hydrophobic character. Because of their poor water solubility, there are extreme difficulties in processing these compounds with the usual pharmaceutical excipients into preparations having sufficient bioavailability.

Generally, cyclosporin-containing medicaments proposed so far are based on the use of an alcohol and/or oils or similar carrier substances in conjunction with one or several surface-active substances. In this way, perorally administrable preparations or also injection preparations are produced.

In e.g. the German Red List 1995 (Rote Liste 1995, Aulendorf), a drink solution is described, which has a content of cyclosporin and ethanol, wherein Labrafil M1944CS or M2125 based on polyoxyethylene-7-glycerol-trioleate or is present as surfactant. This solution additionally contains corn oil or olive oil. The solution is also used to fill gelatin capsules for peroral administration.

A disadvantage of known commercially available cyclosporin preparations for injection is that they are poorly tolerated by some patients owing to the frequent occurrence of anaphylactic reactions (Kahan et al., Lancet, 1984 I: 52; Leunissen, K. M. et al., Lancet, 1985, I: 636).

WO-92/09299 relates to perorally administrable liquid medicaments which contain a cyclosporin with a mixture of a hydrophilic solvent and a surface-active substance in the form of polyoxyethylene-polyoxypropylene block polymers (poloxamers, with a molecular weight of 1000 to 15,500). A disadvantage of these formulations is the precipitation of the active ingredient upon contact with aqueous solutions.

A cyclosporin capsule preparation is also known which contains as carriers and excipients, apart from ethanol and propylene glycol, various corn oil glycerides, glycerin and macrogol-glycerol-hydroxy-stearate, as well as α-tocopherol.

From DE-OS 39 24 207, the contents of which are incorporated herein by reference, cyclosporin-containing preparations are known for intravenous administration, with one or several polyethylene glycol derivatives having the hydroxy-fatty acid moiety bonded in the molecule, together with one or several alcohols as cosolvent. The preferred surfactant in the form of the polyethylene glycol derivative is polyethylene glycol-660-12-hydroxy-stearate. However, a series of other polyethylene glycol derivatives are also disclosed, e.g. polyethylene glycol-9-hydroxy-myristate or polyethylene-glycol-9-hydroxy-palmitate.

The preparations having this composition represent injection concentrates, as disclosed in detail in particular in example 1. These concentrates indicated as drug preparations contain for example 4.85% by weight of cyclosporin A, which when used for intravenous application, has to be diluted prior to the injection with an isotonic solution of saline, glucose, dextran, fructose or mannitol. To the person skilled in the art, it is clear that these concentrates have to be diluted to an extent such that they correspond to the isotonic requirements of injection solutions that are to be administered intravenously (corresponding to the isotonic state of a physiological saline solution). There is no disclosure in this patent specification of a possibility of using these undiluted injection concentrates directly as medicaments or peroral administration.

The preparations described are concerned exclusively with intravenously administrable formulations. The disadvantage of these preparations is that they have to be administered in clinics by trained personnel.

The present applicants have found particularly interesting compositions useful for not only cyclosporins but also macrolides.

Preferred cyclosporins for use in the compositions of this invention are cyclosporin A and ([3'-desoxy-3'-oxo-MeBmt]$^1$-[Val]$^2$-Ciclosporin), the latter disclosed and claimed in EP 296 122.

Rapamycin is an immunosuppressive lactam macrolide produceable, for example by *Streptomyces hygroscopicus*. The structure of rapamycin is given in Kesseler, H., et al.; 1993; *Helv. Chim. Acta*; 76: 117. Rapamycin is an extremely potent immunosuppressant and has also been shown to have antitumor and antifungal activity. Its utility as a pharmaceutical, however, is restricted by its very low and variable bioavailability. Moreover, rapamycin is highly insoluble in aqueous media, e.g. water, making it difficult to formulate stable galenic compositions. Numerous derivatives of rapamycin are known. Certain 16-O-substituted rapamycins are disclosed in WO 94/02136, the contents of which are incorporated herein by reference. 40-O-substituted rapamycins are described in, e.g., in U.S. Pat. No. 5,258,389 and WO 94/09010 (O-aryl and O-alkyl rapamycins); WO 92/05179 (carboxylic acid esters), U.S. Pat. No. 5,118,677 (amide esters), U.S. Pat. No. 5,118,678 (carbamates), U.S. Pat. No. 5,100,883 (fluorinated esters), U.S. Pat. No. 5,151,413 (acetals), U.S. Pat. No. 5,120,842 (silyl ethers), WO 93/11130 (methylene rapamycin and derivatives), WO 94/02136 (methoxy derivatives), WO 94/02385 and WO 95/14023 (alkenyl derivatives) all of which are incorporated herein by reference. 32-O-dihydro or substituted rapamycin are described, e.g., in U.S. Pat. No. 5,256,790, incorporated herein by reference.

Further rapamycin derivatives are described in PCT application number EP96/02441, for example 32-deoxorapamycin as described in Example 1, and 16-pent-2-ynyloxy-32(S)-dihydrorapamycin as described in Examples 2 and 3. The contents of PCT application number EP96/02441 are incorporated herein by reference.

The rapamycin used in the compositions of this invention may be any rapamycin or derivative thereof, for example as disclosed above or in the above-mentioned patent applications.

Thus the rapamycin used in the compositions of this invention may be rapamycin or an O-substituted derivative in which the hydroxyl group on the cyclohexyl ring of rapamycin is replaced by $-OR_1$ in which $R_1$ is hydroxyalkyl, hydroxyalkoxyalkyl, acylaminoalkyl and aminoalkyl; e.g. as described in WO 94/09010, for example 40-O-(2-hydroxy)ethyl-rapamycin, 40-O-(3-hydroxy) propyl-rapamycin, 40-O-[2-(2-hydroxy)ethoxy]ethyl-rapamycin and 40-O-(2-acetaminoethyl)-rapamycin. The rapamycin derivative may be a 26- or 28-substituted derivative.

Preferred rapamycins for use in the compositions of this invention include rapamycin, 40-0-(2-hydroxy)ethyl rapamycin, 32-deoxorapamycin and 16-pent-2-ynyloxy-32 (S)-dihydrorapamycin. A more preferred rapamycin is 40-0-(2-hydroxy)ethyl rapamycin. Numbering of rapamycin derivatives as used herein refers to the structure disclosed as Formula A at page 4 of published PCT application WO 96/13273, the contents of which are incorporated herein by reference.

Ascomycins, of which FK-506 and ascomycin are the best known, comprise another class of lactam macrolides, many of which have potent immunosuppressive and anti-inflammatory activity. FK506 is a lactam macrolide immunosuppressant that is produced by *Streptomyces tsukubaensis* No 9993. The structure of FK506 is given in the appendix to the Merck Index, 11th ed. (1989) as item A5. Ascomycin is described, e.g., in U.S. Pat. No. 3,244,592. Many derivatives of ascomycin and FK-506 have been synthesized, including halogenated derivatives such as 33-epi-chloro-33-desoxy-ascomycin described in EP 427 680. Ascomycin, FK-506 and their structurally similar analogues and derivatives are termed collectively "ascomycins". Examples of compounds of the ascomycin or FK 506 class are those mentioned above. They include for example FK 506, ascomycin and other naturally occurring compounds. They include also synthetic analogues.

A preferred compound of the FK 506 class for use as active ingredient in the present invention is disclosed in EP 427 680, e.g. Example 66a also known as 33-epi-chloro-33-desoxy-ascomycin. Other preferred compounds are disclosed in EP 465 426, and in EP 569 337, e.g. the compound disclosed under Example 6d and Example 71 in EP 569 337. Other preferred compounds include tetrahydropyran derivatives as disclosed in EP 626 385, e.g. the compound disclosed under Example 8 in EP 626 385.

The problem according to the invention comprises formulating pharmaceutical compositions, e.g. cyclosporin or macrolide preparations, which may be administered perorally, have satisfactory bioavailability, low inter-subject and/or intra-subject variability and stability, e.g. in softgels, and in particular can be taken orally by the patient himself.

A solution to this problem surprisingly consists in processing a cyclosporin or macrolide into drug preparations to be administered perorally together with one or more polyethylene glycol derivatives with the hydroxy-fatty acid moiety bonded in the molecule and one or more alcohols as solvent, optionally additionally using fatty acid mono-, di- or triesters and/or the glyceride of ricinoleic acid together with linoleic, palmitic and stearic acid glycerides, as well as ethanol and/or propylene glycols (1,2-propylene glycol as cosolvents or surfactants or carriers).

In one aspect this invention provides a pharmaceutical composition for peroral administration comprising
(a) a cyclosporin or macrolide as active ingredient, and
(b) a polyethoxylated saturated hydroxy-fatty acid.

In another aspect this invention provides a composition containing additionally
(c) a $C_2$–$C_3$-alcohol having one or two hydroxy groups.

In another aspect this invention provides a composition containing additionally
(d) mono-, di- and/or triesters of fatty acids.

In another aspect this invention provides a composition containing additionally
(e) ricinoleic acid glyceride(s) together with smaller proportions of multiply unsaturated fatty acid glycerides or castor oil.

Component b) may be present as sole surfactant.

The composition may consist solely of active ingredient (a), and components (b), (d) and (e).

Components (a), (b) and (c) may be present in a weight ratio of 1 to 4 parts by weight (a): 6 to 15 parts by weight (b): 3 to 12 parts by weight (c).

The bioavailability which may thus be attained is comparable both in respect of the intravenously administrable concentrates, which, upon application, are diluted in a weight ratio of 1:20 to 1:100 with water or with the corresponding solution allowing an isotonic state, and in respect of the commercial preparation of the prior art in the form of solutions or capsule preparations.

Typically the active agent, e.g. the cyclosporin or macrolide, is present in an amount of between about 1 to about 20 wt-%, preferably about 3 to about 15 weight-% based on the weight of the composition.

Polyethoxylated saturated hydroxy fatty acids may be produced by reacting a saturated hydroxy fatty acid with e.g. ethylene oxide or polyethylene glycol. Preferred molecular weights of the polyethoxylated moiety are from 250 to 800 daltons, e.g. 500 to 700.

The fatty acid may be e.g. of 16 to 18 carbon atoms, e.g. C18, e.g. derived from castor oil. The hydroxy group is conveniently attached to a carbon atom located, e.g. from 4 to 8 carbon atoms from a distal methyl group.

The polyethoxylated saturated hydroxy fatty acid may be obtained in conventional manner, e.g. using an appropriate condensation catalyst. The polyethoxylated saturated hydroxy fatty acid may be obtainable by reacting a saturated hydroxy fatty acid with ethylene oxide or with polyethylene glycol. The reaction mixture may contain a mixture of components, e.g. unreacted polyethylene glycol and polyethylene glycol ethers of the hydroxy group.

Saturated hydroxy-fatty acid polyethylene glycol esters suitable for the compositions of this invention are known and commercially available, e.g. from the BASF company under the trade mark Solutol. The saturated hydroxy-fatty acid polyethylene glycol ester component may be present in an amount of between about 15 and 95 weight-%, preferably between 20 and 80 weight-%, and more preferably between about 50 and 75 wt-% based on the weight of the composition.

One Solutol is Solutol® HS 15 which is known, e.g. from BASF technical leaflet MEF 151e (1986), to consist of about 70% polyethoxylated 12-hydroxystearate by weight and about 30% by weight unesterified polyethylene glycol component. Solutol® HS 15 has a hydrogenation value of 90 to 110, a saponification value 53 to 63, acid value maximum 1, and a maximum water content of 0.5% by weight. Solutols, e.g. Solutol HS 15 have been used in injectable compositions.

The alcohol may be a $C_2$–$C_3$-alcohol having one hydroxy group, e.g. ethanol, or two hydroxy groups, e.g. a diol. If present, the alcohol may be in an amount of up to about 40 wt-%, e.g. 5 to 30 wt-% based on the weight of the composition. The alcohol may be substantially anhydrous, e.g. 96% ethanol. The diol may be propylene glycol. A mixture of ethanol and propylene glycol may be present, e.g. in a weight ratio of ethanol to propylene glycol from 2:1 to 1:2, e.g. 1.852 to 1.

The fatty acid mono-, di- and/or triesters may comprise mono-, di- and/or tri-glyceride mixtures, e.g. of linoleic, palmitic and stearic acids, e.g commercially available under the trade mark Cutina, e.g. Cutina MD described in H. P. Fiedler, Lexikon der Hilfsstoffe p.334–335 (1989). If present, the fatty acid mono-, di- and triesters may be in an amount of up to about 60 weight-%, e.g. 20 to about 50 wt-% based on the weight of the composition.

Castor oil may be present in an amount of up to about 30 wt-%, e.g. 10 to 20 wt-%, based on the weight of the composition.

Preferred is a hard gelatin capsule preparation with a filling of 1 part by weight cyclosporin A, 1 part by weight castor oil and 1 part by weight polyethylene glycol-660-12-hydroxy-stearate (for example in the form of Solutol® HS 15) and 2.8 parts by weight fatty acid mono-, di- and triesters (Cutina® MD).

Particularly preferred is a soft gelatin capsule preparation with 5.0 parts by weight cyclosporin A, 65.0 parts by weight polyethylene glycol-660-12-hydroxy-stearate (Solutol HS15 from BASF company) and 28.0 parts by weight 96% ethanol.

Soft gelatin capsules containing compositions of the present invention may be prepared as described for example in published European patent application EP 649 651 the contents of which are incorporated herein by reference.

A formulation for hard gelatin capsules which contains 10.0 parts by weight cyclosporin A, 10.0 parts by weight polyethylene glycol-660-12-hydroxy-stearate and 38.0 parts by weight fatty acid mono-, di- and triesters (Cutina® MD), or a formulation for hard gelatin capsules which are filled with a mixture of 10.0 parts by weight cyclosporin A, 20.0 parts by weight polyethylene glycol-660-12-hydroxy-stearate and 28.0 parts by weight fatty acid mono, di- and triesters (Cutina® MD), have proved to be especially suitable.

[3'-desoxy-3'-oxo-MeBmt]$^1$-[Val]$^2$-Ciclosporin has been found to be effective in reversing multiple drug resistance syndrome.

[3'-desoxy-3'-oxo-MeBmt]$^1$-[Val]$^2$-Ciclosporin and its utility is described in detail in EP 296 122.

The oral compositions of this invention are useful for the known indications of the cyclosporin, or macrolide e.g. rapamycin, e.g. for the following conditions:

a) Treatment and prevention of transplant rejection, e.g. organ or tissue allo- or xeno-transplant rejection, e.g. for the treatment of recipients of e.g. heart, lung, combined heart-lung, liver, kidney, pancreatic, skin or corneal transplants. They are also indicated for the prevention of graft-versus-host disease, such as following bone marrow transplantation.

b) Treatment and prevention of autoimmune disease and of inflammatory conditions, in particular inflammatory conditions with an etiology including an autoimmune component such as arthritis (for example rheumatoid arthritis, arthritis chronica progrediente and arthritis deformans) and rheumatic diseases. Specific autoimmune diseases for which the compounds of the invention may be employed include, autoimmune hematological disorders (including e.g. hemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine ophthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis.

c) Treatment and prevention of asthma.

d) Treatment of multi-drug resistance (MDR). MDR is particularly problematic in cancer patients and AIDS patients who will not respond to conventional chemotherapy because the medication is pumped out of the cells by Pgp. The compositions are therefore useful for enhancing the efficacy of other chemotherapeutic agents in the treatment and control of multidrug resistant conditions such as multidrug resistant cancer or multidrug resistant AIDS.

e) Treatment of proliferative disorders, e.g. tumors, hyperproliferative skin disorder and the like.

f) Treatment of fungal infections.

g) Treatment and prevention of inflammation, especially in potentiating the action of steroids.

h) Treatment and prevention of infection, especially infection by pathogens having Mip or Mip-like factors.

i) Treatment of overdoses of FK-506 and other macrophilin binding immunosuppressants.

The oral compositions of the ascomycin, FK506 or ascomycin derivatives disclosed herein are useful, for example, in the treatment of inflammatory and hyperproliferative skin diseases and of cutaneous manifestations of immunologically-mediated diseases. More specifically, the compositions of this invention are useful as antiinflammatory and as immunosuppressant and antiproliferative agents for use in the prevention and treatment of inflammatory conditions and of conditions requiring immunosuppression, such as a) the prevention and treatment of rejection of organ or tissue transplantation, e.g. of heart, kidney, liver, bone marrow and skin, graft-versus-host disease, such as following bone marrow grafts, autoimmune diseases such as rheumatoid arthritis, systemic lupus erythematosus, Hashimoto's thyroidis, multiple sclerosis, Myasthenia gravis, diabetes type I and uveitis, cutaneous manifestations of immunologically-mediated illnesses;

b) the treatment of inflammatory and hyperproliferative skin diseases, such as psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus and acne; and
c) Alopecia areata.

Where the pharmaceutical composition of this invention is in unit dosage form, e.g. as a tablet, capsule, granules or powder, each unit dosage will suitably contain between 1 mg and 100 mg of the drug substance, more preferably between 10 and 50 mg; for example 15, 20, 25, or 50 mg. Such unit dosage forms are suitable for administration 1 to 5 times daily depending upon the particular purpose of therapy, the phase of therapy and the like.

The exact amount of the compositions to be administered depends on several factors, for example the desired duration of treatment and the rate of release of the active ingredient.

The utility of the pharmaceutical compositions can be observed in standard clinical tests in, for example, known indications of active agent dosages giving equivalent blood levels of active agent; for example using dosages in the range of 1 mg to 1000 mg, e.g. 5 mg to 100 mg, of active agent per day for a 75 kilogram adult and in standard animal models. The increased bioavailability of the drug substance provided by the compositions can be observed in standard animal tests and in clinical trials.

For example an indicated adult daily dose following renal transplantation is from 50 to 200 mg/day.

Other excipients may be present, e.g. microcrystalline cellulose, or $SiO_2$, e.g. Aerosil (H. P. Fiedler) in an amount of up to about 5% by weight, e.g. 1 to 4 wt-%, based on the total weight of the composition.

The dosage form used, e.g. a tablet, may be coated, for example using an enteric coating. Suitable coatings may comprise cellulose acetate phthalate; hydroxypropylmethylcellulose phthalate; a polymethyacrylic acid copolymer, e.g. Eudragit L, S; or hydroxypropylmethylcellulose succinate.

The following examples of formulations according to the invention serve to illustrate the present invention.

EXAMPLES

| | | |
|---|---|---|
| 1. | Cyclosporin A | 100.00 mg |
| | Solutol HS 15 | 660.22 mg |
| | ethanol 96% | 285.20 mg |
| | Aerosil 380 | 45.00 mg |
| | total | 1090.42 mg |
| 2. | cyclosporin A | 100.00 mg |
| | Solutol HS 15 | 500.00 mg |
| | ethanol 96% | 50.00 mg |
| | Aerosil 380 | 30.00 mg |
| | total | 680.00 mg |
| 3. | cyclosporin A | 100.00 mg |
| | Solutol HS 15 | 100.00 mg |
| | Cutina MD | 280.00 mg |
| | castor oil | 100.00 mg |
| | total | 580.00 mg |
| 4. | cyclosporin A | 50.00 mg |
| | Solutol HS 15 | 660.22 mg |
| | ethanol 96% | 185.20 mg |
| | propylene glycol | 100.00 mg |
| | Aerosil 380 | 44.58 mg |
| | total | 1040.00 mg |

Preparation

The compositions of Examples 1 to 4 are prepared whereby the ethanol component (ethanol and/or propylene glycol) is mixed with the Solutol HS 15 and the active ingredient is dissolved therein whilst stirring. A fatty acid mono-, di- and triester, a glyceride of ricinoleic acid and/or a thickener is optionally added to the solution.

The preparations obtained are subsequently filled for example in liquid form into hard or soft gelatin capsules of the desired size, in the desired concentration. The compositions may also be further processed in known manner into tablets. To this end, as described in example 3, the active ingredient is dissolved in a mixture of Solutol HS 15 and castor oil. The solution thus produced is added whilst stirring to the molten component Cutina MD. The liquid melt is poured out, and after solidifying is pulverized in a sifting machine. The granulates obtained are mixed with conventional excipients such as lubricants and liniments, disintegrants, fillers, flavourings etc., and the mixtures pressed into tablets with the desired content of cyclosporin; an example of a conventional excipient is silicon dioxide available commercially under the trade mark Aerosil (Degussa, Germany). If required, the tablets may be coated with specifically desired coatings to improve taste, for aesthetic reasons or to control release of the active ingredient in the intestines, e.g. to control gastric juice resistance or solubility in the small intestine.

Similarly, the liquid melts may be directly filled into blisters.

A group of beagles was used for the experiments and to compare the bioavailability values of the capsule preparations according to the invention. The test preparations were applied perorally to fasted animals using stomach tubes. Blood was taken from the vena saphena of the animals at pre-determined time intervals, and collected in appropriate plastic tubes with an addition of EDTA. The blood samples were stored at −18° C. until used for evaluations. The cyclosporin evaluation was made in whole blood by means of fluorescence polarisation immunoassay (FPIA).

The areas under the curves (AUC), in which the blood levels of the active ingredient are plotted against time, were calculated according to the trapeze rule. The average AUC values of the compositions according to the invention are illustrated in the following table, in a comparison with the commercial preparation of cyclosporin capsules (Sandimmun® Optoral), which were determined in the same reproducible way, at the same dosage, using the same dogs.

| Examples | AUC (0–12 h) ng/ml |
|---|---|
| 1 | 26.555 ± 7.195 |
| 2 | 24.832 ± 10.206 |
| 3 | 17.828 ± 8.193 |
| 4 | 33.109 ± 11.504 |
| cyclosporin capsules (comparison) (Sandimmun ® Optoral) preparation for comparison | 25.469 ± 12.086 |

As the above bioavailability tests show, it is possible using the pharmaceutical compositions according to the invention to make the active ingredient cyclosporin orally available in such a form that its bioavailability corresponds at least to the well known preparations.

It is especially surprising to the person skilled in the art that, in accordance with the invention, only three to at most four excipients and carriers, as well as solubilisers, are sufficient to attain the desired bioavailability. This formulation with very few excipients, which is simplified compared with the preparation for comparison (which contains 6 different components), not only reduces the incompatibilities, but also increases safety of the medicament during production, storage and administration. The latter advantage is especially notable compared with the concentrates known from DE-B-39 24 207, which can only be prepared outside the pharmaceutical industry "in situ" into the dosage form ready for injection, whereby as a result of the required final dilution with special solutions, there is a danger of inaccurate dosages, insterility etc.

With the composition according to the invention, the applicants have succeeded in making available a compact dosage form, for example tablets, with a cyclosporin content, i.e. a medicinal form, which is easy to produce, to handle and to administer, and in addition is economical to produce.

Encapsulation of the formulations into soft gelatin or hard gelatin capsule preparations is effected in conventional manner or by using the process for soft gelatin capsules as described in EP 649651. In a stress test at temperatures of −18° C. to 60° C., the preparations according to the invention did not show any precipitation, decomposition or other changes even after storage for 6 months.

All known natural and synthetic cyclosporins, including the analogues and derivatives thereof, are suitable for use in the preparations according to the invention. Examples of such cyclosporins may be found for example in DE-OS 40 03 844 and DE-OS 40 05 190. Cyclosporin A is preferred.

Compositions containing ([3'-desoxy-3'-oxo-MeBmt]$^1$-[Val]$^2$-Ciclosporin) instead of Cyclosporin A may be prepared in analogous manner to the compositions described in Examples 1 to 4 above.

Compositions containing as active agent rapamycin, 40-0-(2-hydroxy)ethyl rapamycin, 32-deoxorapamycin, 16-pent-2-ynyloxy-32(S)-dihydrorapamycin, 33-epi-chloro-33-desoxy-ascomycin, FK506, the compound disclosed under Example 6d and Example 71 in EP 569 337, or the compound disclosed under Example 8 in EP 626 385 instead of cyclosporin A may be prepared in analogous manner to the compositions described in Examples 1 to 4 above. If desired, the Aerosil may be omitted. The compositions may be encapsulated in soft gels and are stable over, e.g. 2 years.

The concentration of active ingredient in the oral form of administration according to the invention is 20 to 200 mg, preferably 50 to 100 mg per unit dose. References to weight of composition as used herein ignore the weight of any encapsulating medium, e.g. softgel capsule shell.

What is claimed is:

1. A hard gelatin capsule comprising
   (a) a cyclosporin as active ingredient,
   (b) a polyethoxylated saturated hydroxy-fatty acid, and
   (c) a $C_2$–$C_3$ alcohol having one or two hydroxy groups.

2. A hard gelatin capsule of claim 1 wherein the polyethoxylated saturated hydroxy-fatty acid is the sole surfactant.

3. A hard gelatin capsule of claim 1 wherein the cyclosporin is Cyclosporin A.

4. A hard gelatin capsule of claim 1 wherein the polyethoxylated saturated hydroxy-fatty acid comprises polyethylene glycol-660-12-hydroxy-stearate.

5. A hard gelatin capsule of claim 1 wherein the $C_2$–$C_3$ alcohol comprises ethanol, propylene glycol, or ethanol and propylene glycol.

6. A hard gelatin capsule of claim 5 wherein the $C_2$–$C_3$ alcohol comprises ethanol.

7. A hard gelatin capsule of claim 1 wherein the cyclosporin is present in an amount of between 1 to 20 wt-% based on the weight of the composition.

8. A hard gelatin capsule of claim 1 wherein the polyethoxylated saturated hydroxy-fatty acid is present in an amount of between 15 to 95 wt-% based on the weight of the composition.

9. A hard gelatin capsule of claim 1 wherein the $C_2$–$C_3$ alcohol is present in an amount of up to 40 wt-% based on the weight of the composition.

10. A hard gelatin capsule of claim 1 wherein components (a), (b), and (c) are present in the ratio 1 to 4 parts (a): 6 to 15 parts (b): 3 to 12 parts (c), all parts by weight.

* * * * *

UNITED STATES PATENT AND TRADEMARK OFFICE
CERTIFICATE OF CORRECTION

PATENT NO. : 6,951,841 B2
APPLICATION NO. : 09/738212
DATED : October 4, 2005
INVENTOR(S) : Neuer et al.

It is certified that error appears in the above-identified patent and that said Letters Patent is hereby corrected as shown below:

On the title page item (*) should read:

(*) Notice: Subject to any disclaimer, the term of this patent is extended or adjusted under 35 U.S.C. 154(b) by 141 days.

Signed and Sealed this

Tenth Day of June, 2008

JON W. DUDAS
*Director of the United States Patent and Trademark Office*